United States Patent
Brumback et al.

[11] Patent Number: 6,120,504
[45] Date of Patent: Sep. 19, 2000

[54] INTRAMEDULLARY NAIL HAVING DUAL DISTAL BORE FORMATION

[75] Inventors: Robert Brumback, Glyndon, Md.; Robert Border, Bourbon, Ind.

[73] Assignee: Biomet Inc., Warsaw, Ind.

[21] Appl. No.: 09/209,522

[22] Filed: Dec. 10, 1998

[51] Int. Cl.[7] .................................................. A61F 2/28
[52] U.S. Cl. ................................................ 606/62; 606/63
[58] Field of Search ................................ 606/62–68, 105

[56] References Cited

U.S. PATENT DOCUMENTS

| | | |
|---|---|---|
| 2,672,861 | 3/1954 | Jonas et al. . |
| 3,024,785 | 3/1962 | Dobelle . |
| 3,030,951 | 4/1962 | Madarino . |
| 3,710,789 | 1/1973 | Ersek . |
| 3,977,398 | 8/1976 | Burstein . |
| 3,986,564 | 10/1976 | Avila . |
| 4,409,974 | 10/1983 | Freedland . |
| 4,522,202 | 6/1985 | Otte et al. . |
| 4,622,959 | 11/1986 | Marcus ...................................... 606/64 |
| 4,628,920 | 12/1986 | Mathys, Jr. et al. . |
| 4,784,127 | 11/1988 | Mattheck et al. . |
| 4,805,607 | 2/1989 | Engelhardt et al. . |
| 4,827,917 | 5/1989 | Brumfield . |
| 4,858,602 | 8/1989 | Seidel et al. . |
| 4,875,475 | 10/1989 | Conte et al. . |
| 4,911,153 | 3/1990 | Border . |
| 4,928,679 | 5/1990 | Chagneau et al. . |
| 4,946,459 | 8/1990 | Bradshaw et al. . |
| 4,978,349 | 12/1990 | Frigg . |
| 5,035,697 | 7/1991 | Frigg . |
| 5,041,115 | 8/1991 | Frigg et al. . |
| 5,066,296 | 11/1991 | Chapman et al. . |
| 5,112,333 | 5/1992 | Fixel . |
| 5,122,141 | 6/1992 | Simpson et al. . |
| 5,192,281 | 3/1993 | de la Caffiniere . |
| 5,201,733 | 4/1993 | Etheredge, III . |
| 5,201,735 | 4/1993 | Chapman et al. . |
| 5,207,712 | 5/1993 | Cohen . |
| 5,248,313 | 9/1993 | Greene et al. . |
| 5,263,955 | 11/1993 | Baumgart et al. . |
| 5,352,227 | 10/1994 | O'Hara . |
| 5,397,328 | 3/1995 | Behrens et al. . |
| 5,429,640 | 7/1995 | Shuler et al. . |
| 5,441,500 | 8/1995 | Seidel et al. . |
| 5,443,466 | 8/1995 | Shah . |
| 5,489,284 | 2/1996 | James et al. . |
| 5,531,748 | 7/1996 | de la Caffiniere . |
| 5,549,610 | 8/1996 | Russell et al. . |
| 5,569,249 | 10/1996 | James et al. . |
| 5,620,445 | 4/1997 | Brosnahan et al. . |
| 5,626,580 | 5/1997 | Brosnahan et al. . |
| 5,645,545 | 7/1997 | Bryant . |
| 5,653,709 | 8/1997 | Frigg . |
| 5,658,287 | 8/1997 | Hoffmann et al. . |

*Primary Examiner*—Michael Buiz
*Assistant Examiner*—William Lewis
*Attorney, Agent, or Firm*—Michael McNeil

[57] ABSTRACT

An intramedullary nail having dual distal bore formation is comprised of a nail having a longitudinal centerline extending between a distal end and a proximal end. The nail defines a proximal attachment orientation adjacent the proximal end. The nail also defines a left distal bore and a right distal bore adjacent the distal end. The left distal bore and the right distal bore are anteverted in different directions about the longitudinal centerline with respect to the proximal attachment orientation. Thus the same nail can be used in an interlocking, reconstructive or retrograde fashion.

24 Claims, 6 Drawing Sheets

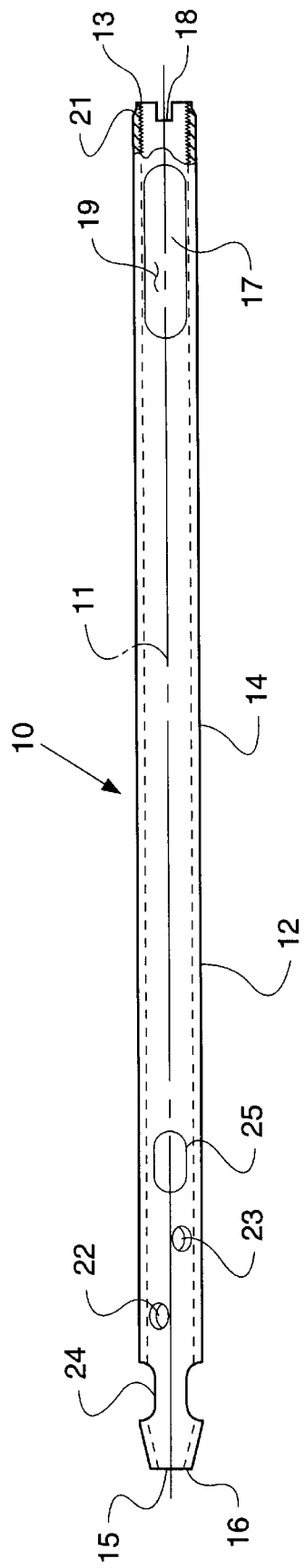

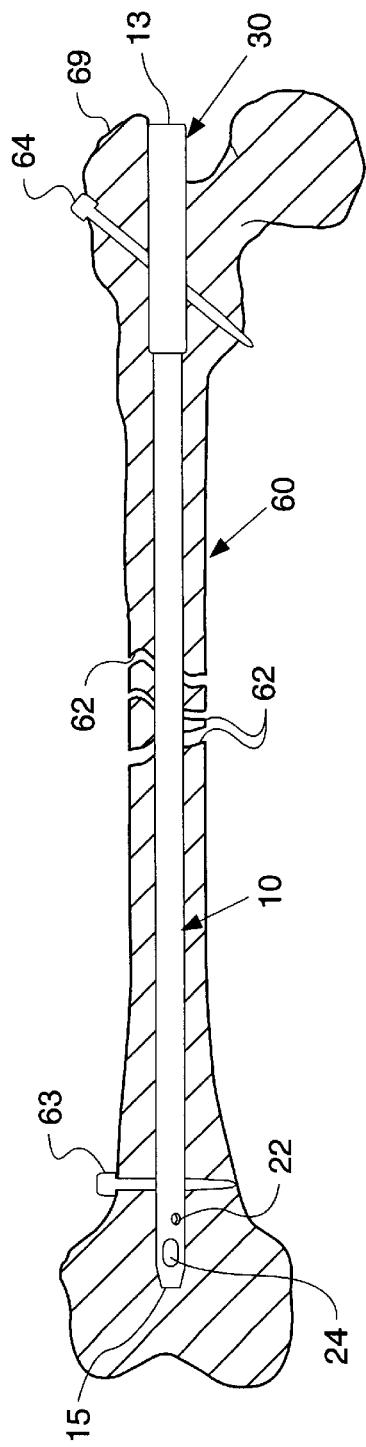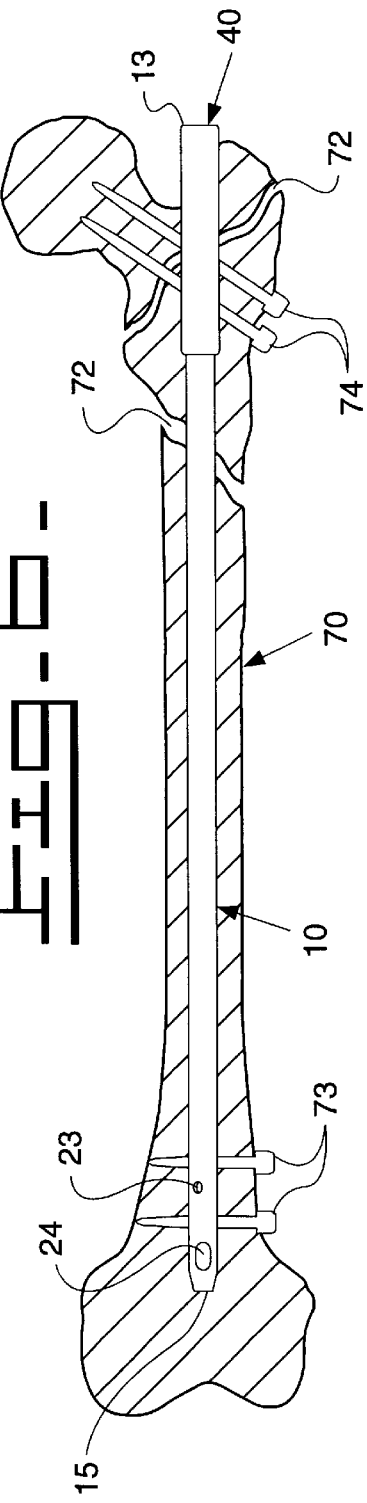

INTRAMEDULLARY NAIL HAVING DUAL DISTAL BORE FORMATION

TECHNICAL FIELD

The present invention relates generally to the treatment of fractures in long bones, and more particularly to an interchangeable intramedullary nail suitable for bone fractures in both left and right side bones.

BACKGROUND ART

It has long been known in the art that fractures in long bones, such as the femur, can be successfully treated through the use of intramedullary nails. The nail is positioned to span the fracture, and often attached on opposite ends directly to the bone. While the fracture is healing, the nail prevents twisting and lateral movement in the fracture area, and carries loads across the fracture that the bone is otherwise unable to support. After the fracture has sufficiently healed, the intramedullary nail may be detached from the bone and sometimes removed from the patient.

Femoral intramedullary nailing is often used to treat traumatic injury. Because of this, hospitals must stock a large number of nails for treatment of all possible patients. Typical nail sets within a hospital inventory include nails with lengths ranging from 32 cm to 46 cm, in 2 cm increments, and nails with diameters ranging from 10 mm to 15 mm, in 1 mm increments. The base number of nails that must be kept in the hospital's inventory is then doubled because most nails within the length and diameter ranges must be stocked for both left and right femoral use. This large number of nails that must be stocked is then increased threefold with the need to stock nails for treatment of first generation nails (as used in interlocking applications), second generation nails (as used in reconstructive applications) and retrograde nails.

One solution to the high inventory requirement of the prior art is for hospitals to stock intramedullary nail systems that utilize modularity to alleviate the need for left and right nails, thereby cutting the number of nails stocked in half. When using a modular system, the surgeon assembles an intramedullary nail from an inventory of base portions and distal portions for either left or right bone treatment at the onset of surgery. While this system reduces the total number of nails that must be kept in stock by hospitals, the actual inventory is only marginally reduced due to the need to stock left and right distal portions for the range of nail diameters. Further, because current nailing systems that utilize modularity to alleviate the need for left and right nails do not address the need for different nails for different fracture treatments (interlocking construction or retrograde), hospitals must still stock a multitude of nails.

The present invention is directed to overcoming one or more of the problems set forth above and to reducing the number of intramedullary nails and attachments that must be inventoried by hospitals.

SUMMARY OF THE INVENTION

An intramedullary nail is comprised of a nail having a longitudinal centerline extending between a distal end and a proximal end. The proximal end of the nail defines a proximal attachment orientation. The distal end of the nail defines a left distal bore and a right distal bore, which are anteverted in different directions about the longitudinal centerline with respect to the proximal attachment orientation.

BRIEF DESCRIPTION OF THE DRAWINGS

FIG. 1 is a side view of an intramedullary nail according to the present invention.

FIG. 5 is a sectioned side view of an intramedullary nail according to the present invention inserted for treatment in a right femur utilizing the interlocking fixation sleeve.

FIG. 6 is a sectioned side view of an intramedullary nail according to the present invention inserted for treatment in a left femur utilizing the reconstructive fixation sleeve.

DETAILED DESCRIPTION OF THE PREFERRED EMBODIMENTS

Figure 1A:
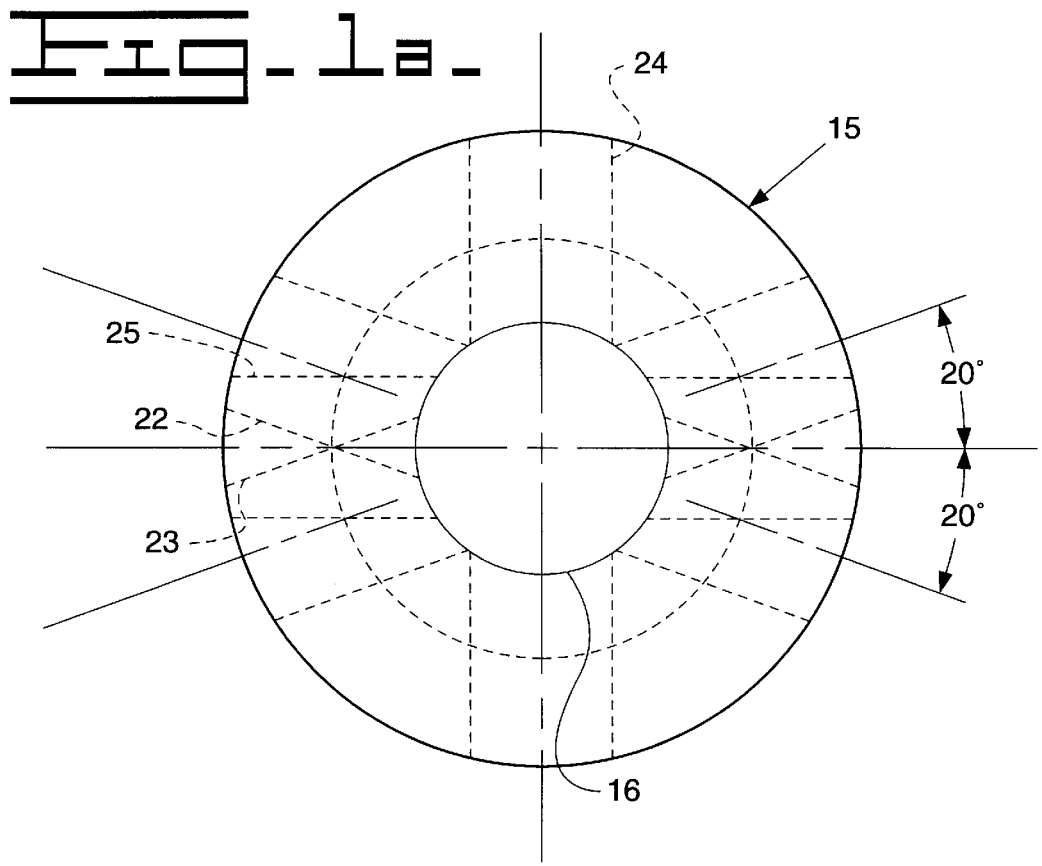
FIG. 1a is an end view of the distal end of the intramedullary nail of FIG. 1.
Figure 1B:
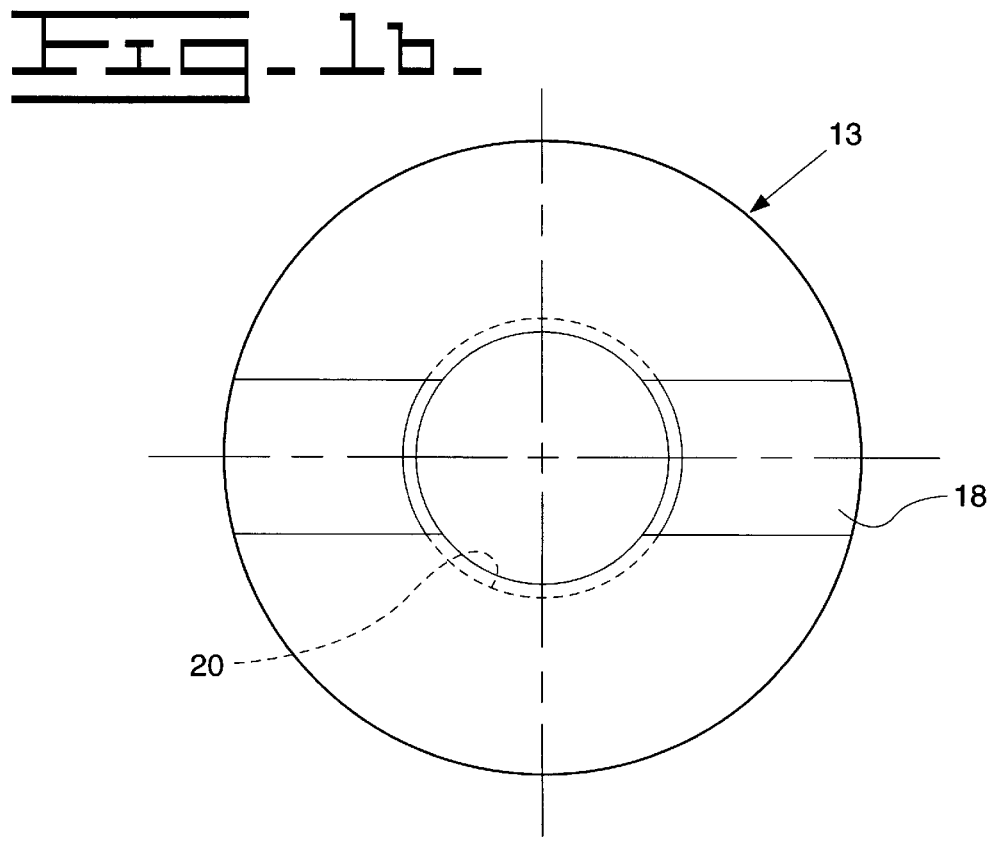
FIG. 1b is an end view of the proximal end of the intramedullary nail of FIG. 1.

Referring now to FIGS. 1, 1a and 1b, an intramedullary nail 10 has a longitudinal centerline 11 and is machined from a suitable metallic alloy, such as titanium, into the shape shown. Intramedullary nail 10 includes a proximal end 13 separated from a distal end 15 by a middle portion 14. For the purposes of this invention, distal end 15 and proximal end 13 of nail 10 are so named regardless of whether nail 10 is to be inserted into the bone in an antegrade or retrograde fashion. A hollow guide bore 16 extends between distal end 15 and proximal end 13 so that nail 10 can be positioned in a bone with the aid of a conventional guide pin. A proximal end slot 17 extends through metallic portion 12 adjacent proximal end 13. A proximal end notch 18, as shown in FIG. 1b, is machined into proximal end 13 and serves as a means to locate the center of slot 17 when the same is hidden from view in a bone. Proximal end notch 18 serves to define a proximal end attachment orientation in this fashion. Except for the relevant portion of hollow guide bore 16, slot 17 is preferably filled with a solid drillable material 19 that is secured to intramedullary nail 10 by any suitable means, such as through the use of molding techniques. A portion of guide bore 16 adjacent proximal end 13 is threaded with internal threads 20, as shown in FIG. 1b, in order to facilitate the attachment of tools during the implantation procedure.

Interlocking of distal end 15 of nail 10 is facilitated by a left distal bore 22, a right distal bore 23, a distal slot 24 and a proximal slot 25. Left distal bore 22 is anteverted plus 20° about longitudinal axis 11 with respect to notch 18, and hence slot 17, while right distal bore 23 is anteverted minus 20° with respect to notch 18 and slot 17 about longitudinal centerline 11. The anteversion of left distal bore 22 and right distal bore 23 with respect to notch 18 is illustrated in FIG. 1a. While 20° is the preferred angle of anteversion for the left and right distal bores 22, 23, a different angle might be desired for other applications. The preferred range for the angle of anteversion for left and right distal bores 22, 23 is between 10° and 35°. The distal end 15 of nail 10 also defines a distal slot 24 and a proximal slot 25 that can also be utilized in attachment of distal end 15 if treatment of the fracture so requires. Distal slot 24 and proximal slot 25 provide the physician with more options and additional flexibility when determining how best to attach intramedullary nail 10 to a bone. Distal slot 24 is preferably oriented at 90° about the longitudinal centerline 11 with respect to the notch 18 and slot 17 while proximal slot 25 is aligned with notch 18 and slot 17. Those skilled in the art will appreciate that the size and orientation of slots 24 and 25 could be varied or eliminated according to preference to provide any desirable level of flexibility to the physician.

Figure 2:
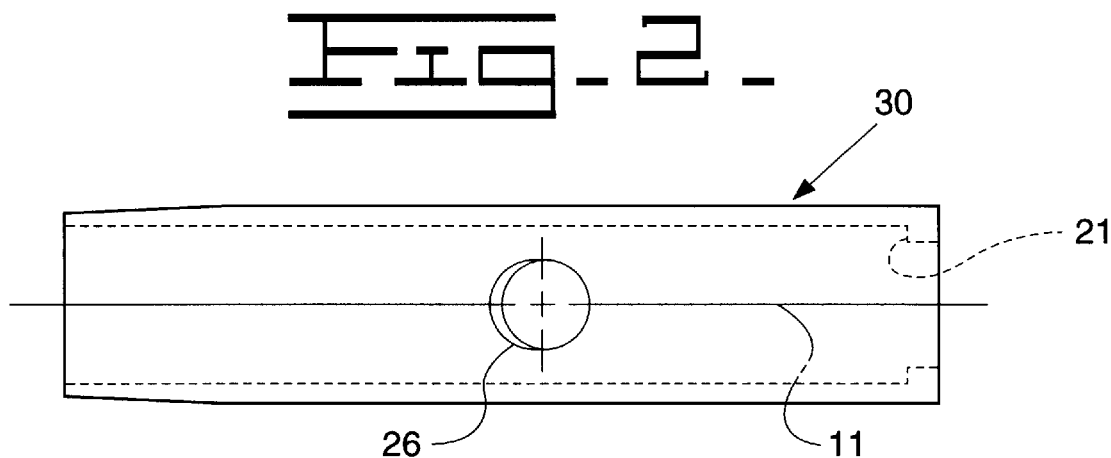
FIG. 2 is a side view of an interlocking sleeve for use on the proximal end of the intramedullary nail of FIG. 1.
Figure 3:
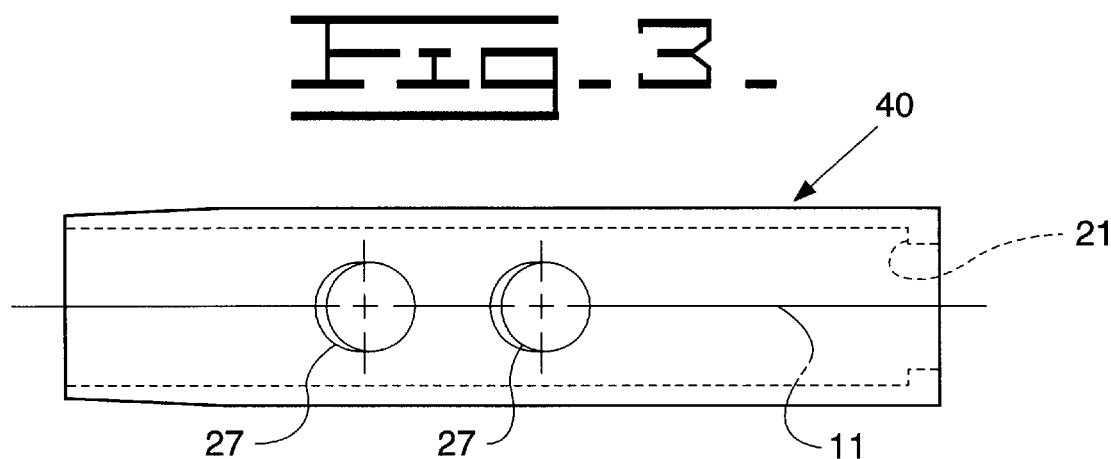
FIG. 3 is a side view of a reconstructive sleeve for use on the proximal end of the intramedullary nail of FIG. 1.
Figure 4:
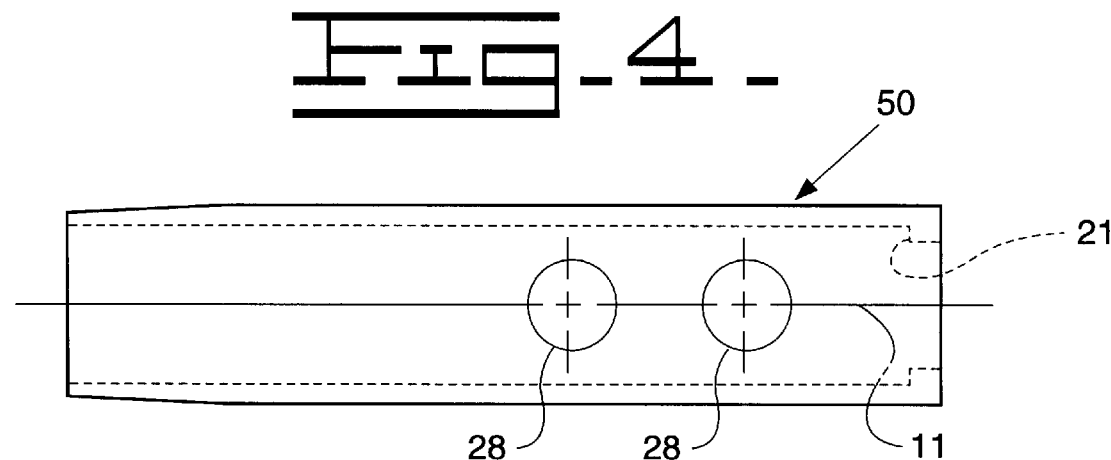
FIG. 4 is a side view of a retrograde sleeve for use on the proximal end of the intramedullary nail of FIG. 1.

Referring now to FIGS. 2–4, there are shown three proximal end sleeves for use on the proximal end 13 of the intramedullary nail 10. FIG. 2 shows an interlocking fixation sleeve 30 that can be used as a first generation nail to repair a fracture. Examples of use for a first generation nail include, but are not limited to, unstable diaphyseal fractures, stable subtrochanteric fractures and distal metaphyseal fractures. Interlocking sleeve 30 has a longitudinal centerline 11 which is concentric with longitudinal centerline 11 of the nail 10 when the interlocking sleeve 30 is fitted over proximal end 13. A shoulder 21 on interlocking sleeve 30 will come in contact with a shoulder 21 on the interlocking sleeve 30 is properly attached. Because of the width of proximal slot 17, the physician has some freedom when orienting interlocking sleeve 30 about nail 10. Interlocking sleeve 30 defines an interlocking sleeve bore 26 which is oriented at about 125° with respect to the longitudinal centerline 11. When interlocking sleeve 30 is fitted over proximal end 13 of nail 10, the interlocking bore 26 is located over slot 17 (FIG. 1).

FIG. 3 shows a reconstructive fixation sleeve 40 that can be used as a second generation nail to repair a fracture. Examples where a second generation nail may be used include, but are not limited to, combined neck-shaft fractures, intertrochanteric fractures and combined intertrochanteric-subtrochanteric fractures. Reconstructive sleeve 40 has a longitudinal centerline 11 which is concentric with longitudinal centerline 11 of nail 10 when the reconstructive sleeve 40 is fitted over proximal end 13. Reconstructive sleeve 40 defines a pair of reconstructive sleeve bores 27 which are oriented at about 125° with respect to the longitudinal centerline 11. When reconstructive sleeve 40 is fitted over the proximal end 13 of nail 10, the reconstructive bores 27 are located over slot 17 (FIG. 1). As with the interlocking sleeve 30, due to the width of slot 17, the physician has some freedom when orienting reconstructive sleeve 40 about nail 10.

FIG. 4 shows a retrograde fixation sleeve 50 that can be used when treating certain fractures better treated in a retrograde fashion. Examples include, but are not limited to, comminuted stable and unstable segmental fractures, supercondylar and intercondylar fractures, and distal fourth fractures. Retrograde sleeve 50 has a longitudinal centerline 11 which is concentric with longitudinal centerline 11 of nail 10 when the retrograde sleeve 50 is fitted over proximal end 13. Retrograde sleeve 50 defines a pair of retrograde sleeve bores 28 which are oriented at 90° with respect to the longitudinal centerline 11. When retrograde sleeve 50 is fitted over the proximal end 13 of nail 10, the retrograde bores 28 are located over slot 17 (FIG. 1). Once again, due to the width of slot 17, the physician has some amount of angular freedom when orienting retrograde sleeve 50 on nail 10.

Referring now to FIG. 5, intramedullary nail 10 is shown according to the present invention inserted for treatment of an unstable diaphyseal fracture 62 in a right femur 60 using interlocking fixation sleeve 30. The implantation procedure is performed in a conventional manner and can be accomplished using known tools, such as the orthopedic surgical instrument taught in U.S. Pat. No. 4,911,153. Nail 10 is inserted into right femur 60 in a conventional manner by first making an incision at the tip of the greater trochanter 69 and extending it proximally in line with the femoral shaft axis. The medullary canal of femur 60 is then reamed using standard reaming techniques and a guide pin is inserted into the reamed canal. Next, a driver bolt is threaded into the proximal end 13 of nail 10 using either an end wrench or a universal socket wrench. Notch 18 (FIG. 1*b*) is then engaged with tangs on the driver bushing to securely lock the assembly and an offset driver is threaded into the driver handle. Nail 10 is then placed over the guide pin and advanced into right femur 60 until proximal end 13 is even with the tip of the greater trochanter 69. Once nail 10 is in its desired position, the guide pin is removed and the offset driver is unthreaded using a lever bar, leaving only the driver handle attached to nail 10. While there are more general ways to describe the tools used in the insertion procedure, those skilled in the art should recognize the conventional manner in which nail 10 is being inserted.

When nail 10 is in position, a proximal screw 64 can be threaded through the interlocking sleeve bore 26, as shown, if required for treatment of the fracture 62. To insert proximal screw 64, a drill bushing is threaded into a guide tube of the driver handle and a drill sleeve is inserted through a proximal target, also located on the driver handle. Conventional fluoroscopic, or interlocking techniques are used to locate targeting sleeve bore 26 for insertion of proximal screw 64. An appropriate drill, here a 5 mm calibrated twist drill, is placed through the drill sleeve and advanced through both cortices. The drill and threaded bushing are then removed from the driver handle. The proximal screw, here a 6.0 mm diameter fully-threaded screw, is next inserted through the guide tube on the driver handle and advanced with a T-wrench until properly seated. Once proximal screw 64 has been driven into interlocking sleeve bore 26, the T-wrench, guide tube and driver handle are removed from nail 10 and an end cap is inserted into proximal end 13.

Once the proximal screw 64 has been inserted and the driver handle has been removed, a distal screw 63 can be advanced through right distal bore 23, as shown. Alternatively distal screw 63 could be inserted into distal slot 24 or proximal slot 25 if needed for treatment of fracture 62. Once again, conventional fluoroscopic, or targeting techniques are used to locate the desired bore 23 or slots 24, 25. A knife blade is then placed on the skin and a 1 cm stab incision is made over the appropriate bore 23 or slot 24, 25 in the nail 10. An appropriately sized drill bit is inserted into the targeting device and the tip of the drill bit is placed into the stab incision such that the tip is centered on the bore 23 or slot 24, 25 in the nail 10. Both cortices are then drilled through and an appropriately sized distal screw 63 is inserted through the bone 60 and the nail 10, using a T-wrench.

While FIG. 5 illustrates the treatment of fracture 62 using the single proximal screw 64 and the single distal screw 63, those skilled in the art will appreciate that variations on the number and placement of the screws 63, 64 are possible for treatment of different kinds of first generation fractures. For example, when treating distal metaphyseal fractures no proximal screw 64 need be inserted in the proximal end 13 of the nail 10. Alternatively, when treating stable subtrochanteric fractures, rather than inserting one distal screw 63 in the right distal bore 23 of nail 10 the surgeon may instead insert no screw 63 in the distal end 15 of nail 10. Another option would be to instead utilize either the distal or proximal slots 24, 25 for distal screw 63 insertion to provide control of rotation and allow for compression of fracture 62. Finally, the surgeon may desire the use of no screws 63, 64, as with treatment of stable diaphyseal fractures.

Referring now to FIG. 6, intramedullary nail 10 is shown according to the present invention inserted for treatment of a combined intertrochanteric-subtrochanteric fracture 72 in a left femur 70 using reconstructive fixation sleeve 40. Nail 10 is inserted into left femur 70 using the reaming and driving techniques described previously. Once nail 10 is in position, a pair of proximal screws 74 can be advanced into the reconstructive sleeve bores 27, as shown, using a slight variation of the drilling technique described for the unstable diaphyseal fracture 62, shown in FIG. 5. After proximal screws 74 have been inserted into proximal end 13, the driver handle can again be removed and an end cap can be inserted. Once this is completed, one or more distal screws 73 can be inserted into left distal bore 22, as shown, or into distal slot 24 or proximal slot 25. The distal screw or screws 73 are inserted in a manner similar to that described for the unstable diaphyseal fracture 62, shown in FIG. 5.

Once again, while FIG. 6 illustrates treatment of the fracture 72 using two proximal screws 74 and the two distal screws 73, it should be appreciated by those skilled in the art that variations on the number and placement of the screws are possible for treatment of a wide array of long bone fractures. For example, when treating intertrochanteric fractures, it may be desirable to not insert any distal screws 73 in the distal end 15 of nail 10. Further, the distal slot 24 and proximal slot 25 (FIG. 1) can be utilized for insertion of additional distal screws 73 to provide better treatment of fracture 72 and/or to create compression.

Figure 7:
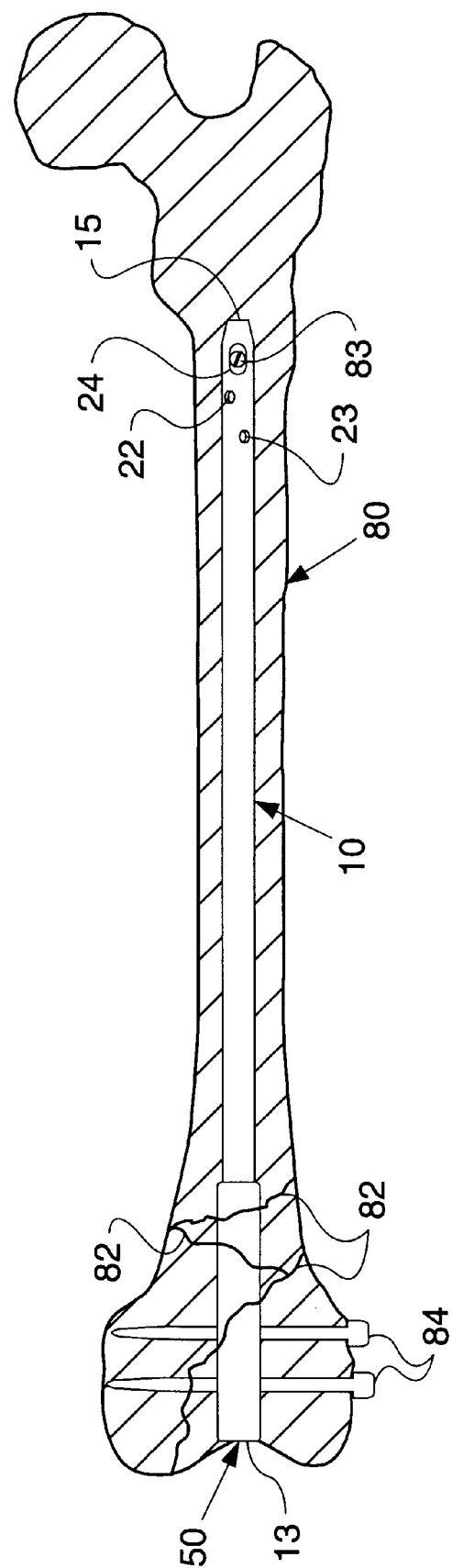
FIG. 7 is a sectioned side view of an intramedullary nail according to the present invention inserted for treatment in a left femur utilizing the retrograde fixation sleeve.

Referring now to FIG. 7, intramedullary nail 10 is shown according to the present invention inserted for treatment of a fracture 82 in left femur 80 using retrograde fixation sleeve 50. Nail 10 is inserted in a conventional manner by first making a longitudinal midline incision from the lower pole of the patella down toward and slightly lateral to the apex of the tibial tubercle. The medullary canal of femur 80 is reamed using standard reaming procedures and a ball tip guide is inserted into the reamed canal. A driver bolt is then passed through the driver bushing and attached to the nail 10. It should be noted again that for the purposes of this invention, distal end 15 and proximal end 13 of nail 10 are so named even though for this particular procedure nail 10 is to be inserted into the femur 80 in a retrograde fashion. Notch 18 (FIG. 1b) of proximal end 13 is then engaged with tangs on the driver bushing to securely lock the assembly. A target arm then engages the driver bushing so that the arm is lateral to the nail 10. This allows the proximal screws 84 to be placed from the lateral to the medial side of the femur. The nail 10 is then inserted by axial pressure and manual twisting until resistance is met. After the nail passes the fracture site, the nail driving guide can be extracted. The nail 10 is in a desirable placement when countersunk approximately 5 mm below the articular surface of the distal femur 80.

With nail 10 in position, proximal screws 84 can then be inserted into the retrograde sleeve bores 28 of proximal end 13, as shown, if required for treatment of the fracture 62. Conventional fluoroscopic or freehand techniques are used to locate retrograde sleeve bores 28 for insertion of proximal screws 84, which are inserted using a modified version of the technique described for treatment of the unstable diaphyseal fracture shown in FIG. 5. Once proximal screws 84 are in place, the driver assembly is removed from nail 10. At this point, one or more distal screws 83 can be driven into left distal bore 22 or into distal slot 24 or proximal slot 25, as shown, if needed for treatment of fracture 82 if distal attachment is desired or needed. Once again, conventional fluoroscopic or targeting techniques are used to locate the desired bore 22 or slots 24, 25, and the screws 83 are inserted in the manner described previously.

Figure 8:
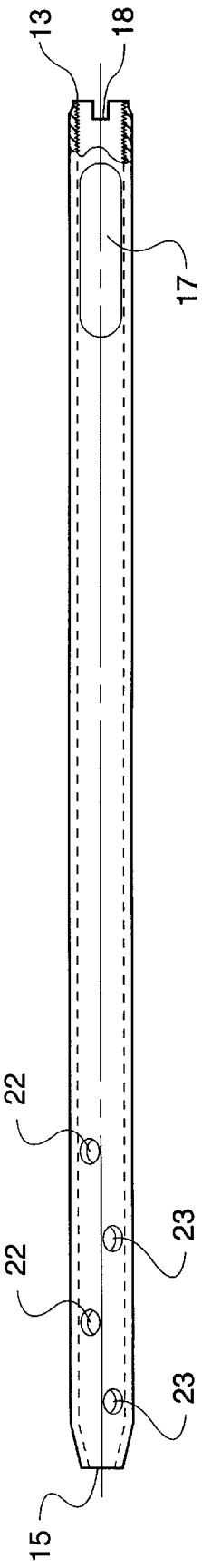
FIG. 8 is a side view of an intramedullary nail according to another embodiment of the present invention.

FIG. 8 illustrates another embodiment of the present invention. In this embodiment, distal end 15 defines a pair of left distal bores 22 and right distal bores 23. The pair of left distal bores 22 are anteverted plus 20° about longitudinal centerline 11 with respect to notch 18 and slot 17, while the pair of right distal bores 23 are anteverted minus 20° about longitudinal centerline 11 with respect to notch 18 and slot 17.

It should be understood that the above description is intended for illustrative purposes only, and is not intended to limit the scope of the present invention in any way. For instance, although nail 10 is shown in FIG. 1 as not having a bow, those skilled in the art will appreciate that bowed nails could be used to better fit the internal contours of the bone. While the present invention is described for use in a human femur, it should be appreciated by those skilled in the art that this invention could be used for treatment on any human bone for which a different intramedullary nail must be used for left and right limbs. Additionally, while the nail 10 has been illustrated as being inserted into a reamed canal (FIGS. 5–7), the nail 10 could instead be inserted in an unreamed canal if desired by the surgeon. Further, while the present invention utilizes proximal end sleeves to allow fractures to be treated using of first generation, second generation and retrograde nails, it should be appreciated that other attachments could be substituted in place of the sleeves, or that the sleeves could be omitted all together. It should also be appreciated by those skilled in the art that this invention could be used for veterinary medicine applications and not exclusively for treatment of fractures in human bones. Thus, various modifications could be made without departing from the intended spirit and scope of the invention as defined by the claims below.

What is claimed is:

1. An intramedullary nail comprising:
    a nail having a longitudinal centerline extending between a distal end and a proximal end;
    said nail defining a proximal attachment orientation adjacent said proximal end;
    said nail defining a left distal bore and a right distal bore adjacent said distal end; and
    said left distal bore and said right distal bore being anteverted at angles with a magnitude greater than zero degrees in different directions about said longitudinal centerline with respect to said proximal attachment orientation.

2. The intramedullary nail of claim 1 wherein said left distal bore is oriented at an angle greater than plus 10° and less than plus 35° about said longitudinal centerline with respect to said proximal attachment orientation; and
    said right distal bore is oriented at an angle greater than minus 10° and less than minus 35° about said longitudinal centerline with respect to said proximal attachment orientation.

3. The intramedullary nail of claim 1 wherein said nail defines at least one distal slot adjacent said distal end.

4. The intramedullary nail of claim 3 wherein said at least one distal slot is oriented at an angle greater than zero degrees with respect to said left distal bore and said right distal bore about said longitudinal centerline.

5. The intramedullary nail of claim 3 wherein said at least one distal slot includes a first distal slot oriented at about 90° with respect to a second distal slot.

6. The intramedullary nail of claim 5 wherein said first distal slot is oriented with respect to said left distal bore and said right distal bore at an angle greater than 55° and less than 80° about said longitudinal centerline; and said second distal slot is oriented with respect to said left distal bore and said right distal bore at an angle greater than 10° and less than 35° about said longitudinal centerline.

7. The intramedullary nail of claim 1 further comprising a proximal end fixation attachment, said proximal end fixation attachment being chosen from the group consisting essentially of an interlocking fixation attachment, a reconstructive fixation attachment or a retrograde fixation attachment.

8. An intramedullary nail comprising:

a nail having a longitudinal centerline extending between a distal end and a proximal end;

said nail defining a proximal attachment orientation adjacent said proximal end;

said nail defining a left distal bore and a right distal bore adjacent said distal end; and said left distal bore and said right distal bore being anteverted in different directions at angles with a magnitude of at least 10° about said longitudinal centerline with respect to said proximal attachment orientation.

9. The intramedullary nail of claim 8 wherein said nail defines at least one distal slot adjacent said distal end.

10. The intramedullary nail of claim 9 wherein said at least one distal slot is oriented about said longitudinal centerline at an angle with respect to said left distal bore and said right distal bore.

11. The intramedullary nail of claim 10 wherein said at least one distal slot is oriented about said longitudinal centerline with respect to said left distal bore and said right distal bore at an angle greater than 10° and less than 35°.

12. The intramedullary nail of claim 9 wherein said at least one distal slot includes a first distal slot oriented at about 90° with respect to a second distal slot.

13. The intramedullary nail of claim 12 wherein said first distal slot is oriented with respect to said left distal bore about said longitudinal centerline at an angle greater than 55° and less than 80°; and said second distal slot is oriented with respect to said right distal bore about said longitudinal centerline at an angler greater than 10° and less than 35°.

14. The intramedullary nail of claim 8 further comprising a proximal end fixation attachment, said proximal end fixation attachment being chosen from the group consisting essentially of an interlocking fixation attachment, a reconstructive fixation attachment, or a retrograde fixation attachment.

15. An intramedullary nail comprising:

a nail having a longitudinal centerline extending between a distal end and a proximal end;

said nail defining a proximal attachment orientation adjacent to said proximal end; and said nail defining a set of four openings adjacent said distal end, each of said four openings having a different angular orientation with respect to said proximal attachment orientation.

16. The intramedullary nail of claim 15 wherein said set of four openings adjacent said distal end includes a left distal bore, a right distal bore, a distal slot and a proximal slot.

17. The intramedullary nail of claim 16 wherein said distal slot is oriented with respect to said proximal attachment orientation at an angle of 90° about said longitudinal centerline; and said proximal slot is oriented with respect to said proximal attachment orientation at an angle of 0° about said longitudinal centerline.

18. The intramedullary nail of claim 17 wherein said left distal bore and said right distal bore are anteverted in different directions at about 20° about said longitudinal centerline with respect to said proximal attachment orientation.

19. The intramedullary nail of claim 18 wherein said distal slot is oriented with respect to said left distal bore and said right distal bore at an angle of 70° about said longitudinal centerline; and said proximal slot is oriented with respect to said left distal bore and said right distal bore at an angle of 20° about said longitudinal centerline.

20. The intramedullary nail of claim 19 further comprising a proximal end fixation attachment, said proximal end fixation attachment being chosen from the group consisting essentially of an interlocking fixation attachment, a reconstructive fixation attachment or a retrograde fixation attachment.

21. An intramedullary nail for use in one of a right femur and a left femur exhibiting similar anteversion of the necks thereof comprising:

a nail having a longitudinal centerline extending between a distal end and a proximal end;

said nail defining a proximal attachment orientation adjacent said proximal end;

said nail defining a left distal bore and a right distal bore adjacent said distal end; and said left distal bore and said right distal bore extending at different angles about said longitudinal centerline with respect to said proximal attachment orientation such that selective placement of said nail in the left femur or the right femur with the corresponding said left distal bore or said right distal bore extending generally from the lateral side to the medial side of the femur results in proper anteversion of the proximal attachment orientation.

22. The intramedullary nail of claim 21 in which said left distal bore and said right distal bore both extend generally perpendicular to said longitudinal centerline.

23. The intramedullary nail of claim 21 in which the respective angular orientations of said left distal bore and said right distal bore relative said proximal attachment orientation are at generally equal but opposite anteversion angles.

24. The intramedullary nail of claim 23 in which the equal but opposite anteversion angles are between 10 and 35 degrees.

* * * * *